(12) United States Patent
Abe

(10) Patent No.: US 6,940,641 B2
(45) Date of Patent: Sep. 6, 2005

(54) FLUORESCENCE OBSERVATION APPARATUS

(75) Inventor: Katsuyuki Abe, Hachioji (JP)

(73) Assignee: Olympus Corporation, Tokyo (JP)

( * ) Notice: Subject to any disclaimer, the term of this patent is extended or adjusted under 35 U.S.C. 154(b) by 122 days.

(21) Appl. No.: 10/714,657

(22) Filed: Nov. 18, 2003

(65) Prior Publication Data

US 2005/0103973 A1 May 19, 2005

(51) Int. Cl.$^7$ .............................. G02B 21/06
(52) U.S. Cl. .................... 359/385; 250/458.1
(58) Field of Search ................. 359/368, 381, 359/385, 387, 388, 389; 250/458.1, 459.1, 461.1

(56) References Cited

U.S. PATENT DOCUMENTS

| | | | | |
|---|---|---|---|---|
| 5,296,703 A | * | 3/1994 | Tsien | 250/235 |
| 5,710,663 A | * | 1/1998 | Kawasaki | 359/389 |
| 5,719,391 A | * | 2/1998 | Kain | 250/235 |
| 6,865,021 B2 | * | 3/2005 | Koyama | 359/381 |

* cited by examiner

*Primary Examiner*—Mark A. Robinson
(74) *Attorney, Agent, or Firm*—Kenyon & Kenyon

(57) ABSTRACT

A fluorescence observation apparatus includes a light source, an illumination optical system conducting irradiation light from the light source to a specimen, an aperture member provided in the illumination optical system, a first wavelength selective member, a light splitter deflecting the irradiation light to conduct the light to the specimen, an objective lens interposed between the light splitter and the specimen, a second wavelength selective member transmitting fluorescent light emanating from the specimen, a detecting device receiving the fluorescent light, and a projection optical system projecting the aperture member at the pupil position of the objective lens. In this case, the aperture member has a partial aperture through which part of the irradiation light passes, and the size of the partial aperture and the magnification of the projection optical system are set to satisfy the following Conditions:

$$0.5NA \leq NA_1 < NA$$

$$NA_1 < n$$

where $NA_1$ is a numerical aperture derived from an angle made by a ray closest to the optical axis, of rays of light passing through the partial aperture, with the optical axis on the specimen, NA is the maximum numerical aperture of the objective lens, and n is the refractive index of a medium holding the specimen.

10 Claims, 8 Drawing Sheets

PART OF AUTO FLUORESCENCE

FLUORESCENCE OBSERVATION APPARATUS

BACKGROUND OF THE INVENTION

1. Field of the Invention

This invention relates to a fluorescence observation apparatus used to irradiate a specimen with light and to detect light emanating from the specimen, especially fluorescent light.

2. Description of Related Art

Recently, in biology, researches that use specimens in which a biological function is not retained, but a living condition is maintained has been widely conducted. Specifically, a fluorescent molecule is peculiarly bonded to a remarkable, particular protein molecule, and a fluorescence microscope is used to observe and analyze the behavior and distribution of these molecules so that biological functions are clarified. In addition to this, with the advent of GFP (green fluorescent protein) in recent years, it has become possible to produce fluorescent protein in a cell so that the observation and analysis can be made in a state where more physiological activity is held.

"GFP and bioimaging" (Experiment Medicine, separate volume; Experiment Lecture 3 of Postgenome Age, Yodosha, page 156, 2000) gives the description that it is important that, in order to maintain a state of cellular physiological activity, as an imaging point of a living cell, excitation light for irradiating a specimen is rendered as faint as possible by an attenuation filter and fluorescent light emanating from the specimen is fully utilized, that is, a high-sensitivity fluorescence observation with a high SIN ratio is carried out.

Each of Japanese Patent Kokai Nos. Hei 03-269405, Hei 10-96862, and Hei 10-227980 discloses a technique that aims at a high-sensitivity fluorescence microscope.

The technique disclosed in Kokai No. Hei 03-269405 is such that irradiation light from a light source is converted into annular light and a specimen is irradiated with this light that fails to pass through an objective lens. As an example where an immersion objective lens having a numerical aperture greater than 1.0 is used, the technique disclosed in Kokai No. Hei 10-227980 is known. In the technique disclosed in Kokai No. Hei 10-96862, a reflecting mirror is placed so that part of fluorescent light emanating from a specimen is blocked, and irradiation light from a light source is reflected toward the specimen by this reflecting mirror.

SUMMARY OF THE INVENTION

The fluorescence observation apparatus of the present invention includes a light source, an illumination optical system conducting irradiation light from the light source to a specimen, an aperture member provided in the illumination optical system, a first wavelength selective member, a light splitter deflecting the irradiation light to conduct the light to the specimen, an objective lens interposed between the light splitter and the specimen, a second wavelength selective member transmitting fluorescent light emanating from the specimen, and a detecting device receiving the fluorescent light. In this case, the aperture member has a partial aperture through which part of the irradiation light passes, and the fluorescence observation apparatus is provided with a projection optical system projecting the aperture member at the pupil position of the objective lens. The size of the partial aperture and the magnification of the projection optical system are set to satisfy the following Conditions (1) and (2):

$$0.5NA \leq NA_1 < NA \quad (1)$$

$$NA_1 < n \quad (2)$$

where $NA_1$ is a numerical aperture derived from an angle made by a ray closest to the optical axis, of rays of light passing through the partial aperture, with the optical axis on the specimen, NA is the maximum numerical aperture of the objective lens, and n is the refractive index of a medium holding the specimen.

According to the present invention, the shape of the partial aperture is preferably annular.

In the fluorescence observation apparatus of the present invention, the size of the partial aperture and the magnification of the projection optical system are set to satisfy the following Condition (1'), instead of Condition (1), and the following Condition (3):

$$0.5NA \leq NA_1 < 0.95NA \quad (1')$$

$$NA_1 < NA_2 \leq NA \quad (3)$$

where $NA_2$ is a numerical aperture derived from an angle made by a ray farthest from the optical axis, of rays of light passing through the partial aperture, with the optical axis on the specimen.

The fluorescence observation apparatus of the present invention, when satisfying Conditions (1) and (2), preferably satisfies the following Condition (1") instead of Condition (1):

$$0.75NA \leq NA_1 < NA \quad (1'')$$

The fluorescence observation apparatus of the present invention, when satisfying Conditions (1') and (3), preferably satisfies the following Condition (4):

$$NA_2 < n \quad (4)$$

The fluorescence observation apparatus of the present invention, when satisfying Conditions (1) and (2), preferably satisfies the following Condition (5):

$$0.1 \leq NA_2 - NA_1 \quad (5)$$

In the fluorescence observation apparatus of the present invention, the objective lens preferably has a numerical aperture greater than 1.0.

In the fluorescence observation apparatus of the present invention, the objective lens preferably has a numerical aperture greater than 1.35.

The fluorescence observation apparatus of the present invention is constructed so that the aperture member is preferably movable in and out of the illumination optical system.

The fluorescence observation apparatus of the present invention includes a light source, an illumination optical system conducting irradiation light from the light source to a specimen, an aperture member provided in the illumination optical system, a first wavelength selective member, and a light splitter deflecting the irradiation light to conduct the light to the specimen. In this case, the aperture member has a partial aperture passing part of the irradiation light, and a projection optical system projecting the aperture member at the pupil position of the objective lens is provided. The size of the partial aperture and the magnification of the projection optical system are set to satisfy Conditions (1) and (2).

According to the present invention, auto fluorescence produced from the objective lens can be held to a minimum and at the same time, the intensity of excitation light can be rendered very low. This offers a fluorescence observation apparatus that is most suitable for the clarification of biological functions of living cells and has an extremely high sensitivity.

These and other features and advantages of the present invention will become apparent from the following detailed description of the preferred embodiments when taken in conjunction with the accompanying drawings.

DETAILED DESCRIPTION OF THE PREFERRED EMBODIMENTS

Figure 1:
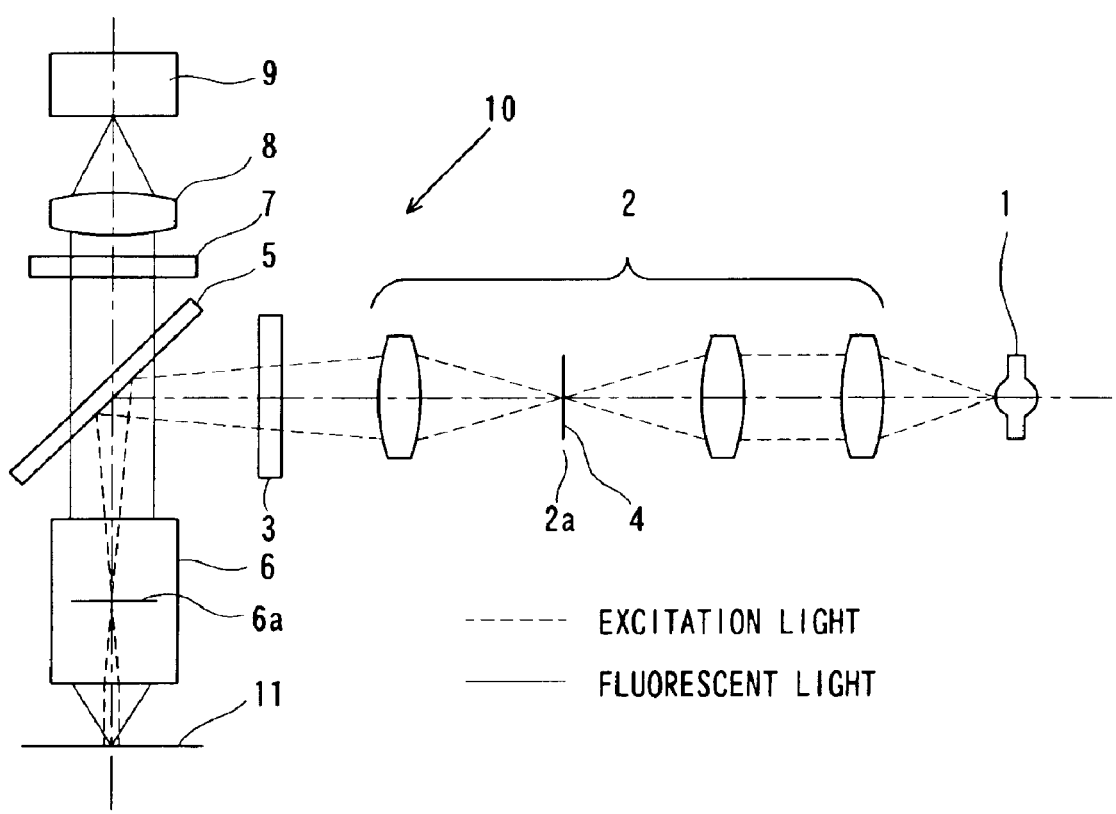
FIG. 1 is a view showing the entire construction of the fluorescence observation apparatus of the present invention.

The fluorescence observation apparatus of the present invention includes a light source, an illumination optical system conducting irradiation light from the light source to a specimen, an aperture member provided in the illumination optical system, a first wavelength selective member, a light splitter deflecting the irradiation light to conduct the light to the specimen, an objective lens interposed between the light splitter and the specimen, a second wavelength selective member transmitting fluorescent light emanating from the specimen, and a detecting device receiving the fluorescent light.

The aperture member has a partial aperture through which part of the irradiation light passes. Whereby, the fluorescence observation apparatus is such that the irradiation light does not pass through the entire surfaces (the entire pupil) of individual lens elements constituting the objective lens. That is, the irradiation light is restricted so that it passes through only a part of the area of each lens element. Consequently, the production of auto fluorescence in each lens element can be minimized.

A projection optical system projecting the aperture member at the pupil position of the objective lens is provided, and the size of the partial aperture and the magnification of the projection optical system are set to satisfy the following Conditions (1) and (2):

$$0.5NA \leq NA_1 < NA \quad (1)$$

$$NA_1 < n \quad (2)$$

where $NA_1$ is a numerical aperture derived from an angle made by a ray closest to the optical axis (hereinafter called an inner ray), of rays of light passing through the partial aperture, with the optical axis on the specimen, NA is the maximum numerical aperture of the objective lens, and n is the refractive index of a medium holding the specimen.

In the present invention, as mentioned above, the irradiation light is restricted by the aperture member. The above conditions determine the area of the objective lens through which the restricted irradiation light should pass where it travels through the objective lens. Condition (1) determines that the inner ray should pass through an area more than a half of the maximum numeral aperture of the objective lens. Below the lower limit of Condition (1), the irradiation light passes through the area of a thin lens part, and thus the amount of production of the auto fluorescence is increased. Beyond the upper limit of Condition (1), the irradiation light ceases to be incident on the objective lens, and hence the irradiation light fails to reach the specimen.

Condition (2) determines that the inner ray is not totally reflected by the surface of the specimen. If Condition (2) is not satisfied, the irradiation light (the inner ray) will undergo total reflection, and therefore the specimen ceases to be irradiated with the irradiation light. Also, total reflection by the surface of the specimen refers to total reflection caused by an interface between the medium holding the specimen and a cover glass.

In the fluorescence observation apparatus of the present invention disclosed above, the shape of the partial aperture is annular. Whereby, the specimen can be uniformly illuminated from all directions (360°) and thus nonuniformity of illumination is not caused.

In the fluorescence observation apparatus of the present invention disclosed above, the size of the partial aperture and the magnification of the projection optical system are set to satisfy the following Condition (1'), instead of Condition (1), and the following Condition (3):

$$0.5NA \leq NA_1 < 0.95NA \quad (1')$$

$$NA_1 < NA_2 \leq NA \quad (3)$$

where $NA_2$ is a numerical aperture derived from an angle made by a ray farthest from the optical axis (hereinafter called an outer ray), of rays of light passing through the partial aperture, with the optical axis on the specimen.

Condition (1'), like Condition (1), determines the passage area of the inner ray. Here, beyond the upper limit of Condition (1'), the amount of illumination light cannot be sufficiently ensured. Alternatively, the illumination light ceases to reach the specimen. Condition (3) determines the passage area of the outer ray. Here, it is optically impossible to overstep the lower limit of Condition (3). Beyond the upper limit of Condition (3), illumination light that is not incident on the objective lens becomes copious, thus causing the shortage of the amount of light.

When the fluorescence observation apparatus satisfies Conditions (1) and (2), it is desirable to further satisfy the following Condition (1") instead of Condition (1):

$$0.75NA \leq NA_1 < NA \quad (1")$$

When Condition (1") is satisfied, the inner ray is to pass through a farther periphery of the objective lens. Consequently, the production of auto fluorescence can be suppressed.

When the fluorescence observation apparatus satisfies Conditions (1') and (3), it is desirable to further satisfy the following Condition (4):

$$NA_2 < n \quad (4)$$

When Condition (4) is satisfied, the outer ray is also not totally reflected. Thus, since the specimen is irradiated with all of the irradiation light reaching the specimen, efficient illumination can be provided. Moreover, since totally reflected light is not produced, only fluorescent light reaches the detecting device. Hence, a fluorescent image with good contrast is obtained.

As seen from Conditions (1') and (3), when the difference between the numerical apertures $NA_2$ and $NA_1$ is 0.05, the amount of illumination light required to obtain the fluorescent image can be ensured. However, in order to obtain a better fluorescent image, it is desirable to satisfy the following Condition (5) in addition to satisfying Conditions (1) and (2):

$$0.1 \leq NA_2 - NA_1 \tag{5}$$

It is desirable that the objective lens has a numerical aperture greater than 1.0. It is more desirable that the objective lens has a numerical aperture greater than 1.35. By doing so, a thinner-lens area can be thought of as the passage area of the irradiation light, and thus the production of auto fluorescence can be suppressed.

It is desirable that the aperture member is designed to be movable in and out of the illumination optical system. By doing so, different irradiation techniques are used, and therefore illumination according to an observation system can be made.

Also, in the present invention, the partial aperture of the aperture member is projected at the pupil position of the objective lens by the projection optical system interposed between the aperture member and the pupil position of the objective lens. Therefore, the outer ray refers to "a ray intersecting with the optical axis on the specimen after passing through the most outer portion of a projected image of the partial aperture". When the outside diameter of the projected image of the partial aperture is denoted by D1 and the focal length of the objective lens is denoted by f, $NA_1 = D1/2f$. Similarly, the inner ray refers to "a ray intersecting with the optical axis on the specimen after passing through the most inner portion of a projected image of the partial aperture". When the inside diameter of the projected image of the partial aperture is denoted by D2, $NA_2 = D2/2f$.

Also, although an upright microscope shown in FIG. 1 can be constructed as one unit, it can also be constructed as a plurality of subunits provided in accordance with functions. In this case, illumination subunits (a fluorescence illumination apparatus) can be realized in such a way as described below.

The fluorescence illumination apparatus includes a light source, an illumination optical system conducting irradiation light from the light source to a specimen, an aperture member provided in the illumination optical system, a first wavelength selective member, and a light splitter deflecting the irradiation light to conduct the light to the specimen. In this case, the aperture member has a partial aperture through which part of the irradiation light passes, and the fluorescence illumination apparatus is provided with a projection optical system projecting the aperture member at the pupil position of the objective lens. The size of the partial aperture and the magnification of the projection optical system are set to satisfy Conditions (1) and (2).

By using this construction, the fluorescence observation apparatus that is capable of carrying out a high-sensitivity fluorescence observation can be provided. The fluorescence illumination apparatus satisfies the conditions discussed about the fluorescence observation apparatus.

In accordance with the embodiments, the present invention will be explained in detail below.

First Embodiment

Figure 2:
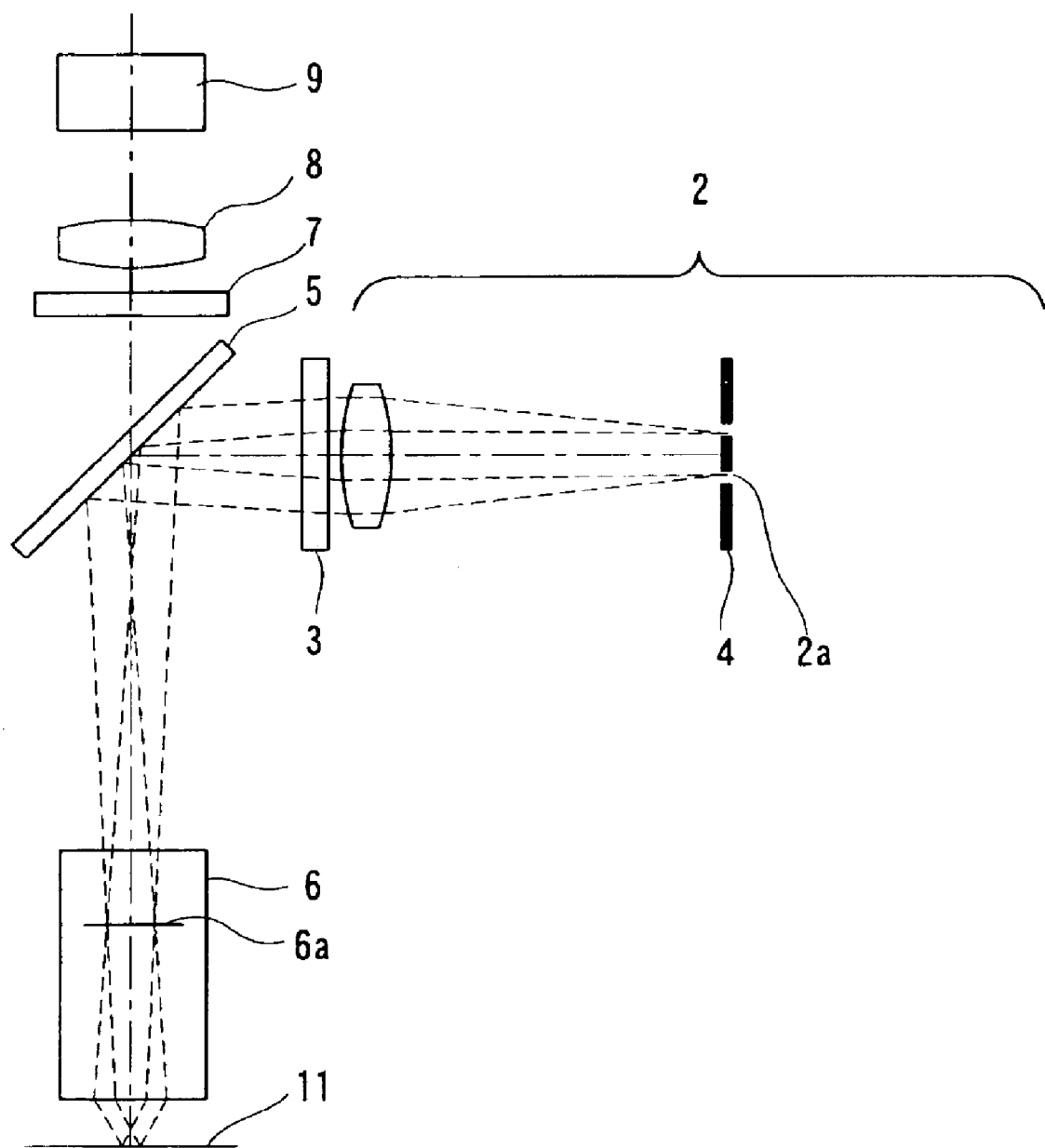
FIG. 2 is a view showing a state of light emerging from an aperture member.

The fluorescence observation apparatus of the first embodiment in the present invention is shown in FIGS. 1 and 2. The fluorescence observation apparatus of the first embodiment has the upright microscope as its basic construction. In FIG. 1, an upright microscope 10 includes a light source 1, an illumination optical system 2, a first wavelength selective member 3, an aperture member 4, a light splitter 5, an objective lens 6, a second wavelength selective member 7, an imaging lens 8, and a detecting device 9. As the light source 1, for example, an extra-high pressure mercury lamp or a xenon lamp is used. Light emitted from the light source 1 contains light extending from the ultraviolet region to the visible region and near-infrared light.

The light from the light source 1 passes through the illumination optical system 2 and is incident on the first wavelength selective member 3. The illumination optical system 2 is constructed with a plurality of lenses. A conjugate position (designated by 2a) relative to a pupil position 6a of the objective lens 6 lies in this optical system. At the conjugate position 2a, the aperture member 4 is located.

The first wavelength selective member 3 is an optical element, usually called an excitation filter, and has preset spectral transmittance characteristics. The first wavelength selective member 3 is placed in the optical path and thereby can be transparent to only light in a preset wavelength region, of the light extending from the ultraviolet region to the visible region. Light emerging from the first wavelength selective member 3 (hereinafter called excitation light) is then incident on the light splitter 5.

The light splitter 5 is placed so that its reflecting surface makes an angle of 45° with the optical axis of the illumination optical system. It has the spectral transmittance characteristics that most of the excitation light is reflected and most of fluorescent light to be described later is transmitted. The excitation light incident on the light splitter 5 is thus reflected toward the objective lens 6. Also, in the first embodiment, a lens constituting the illumination optical system 2 is interposed between the aperture member 4 and the objective lens 6. As such, this lens corresponds to the projection optical system.

The excitation light irradiates a specimen 11 through the objective lens 6. In the specimen 11, fluorescent light is produced by the excitation light. Part of the excitation light is reflected by the specimen 11. The fluorescent light and the excitation light pass through the objective lens 6 to enter the light splitter 5. Most of the fluorescent light passes through the light splitter 5 and is incident on the second wavelength selective member 7.

Figure 3:
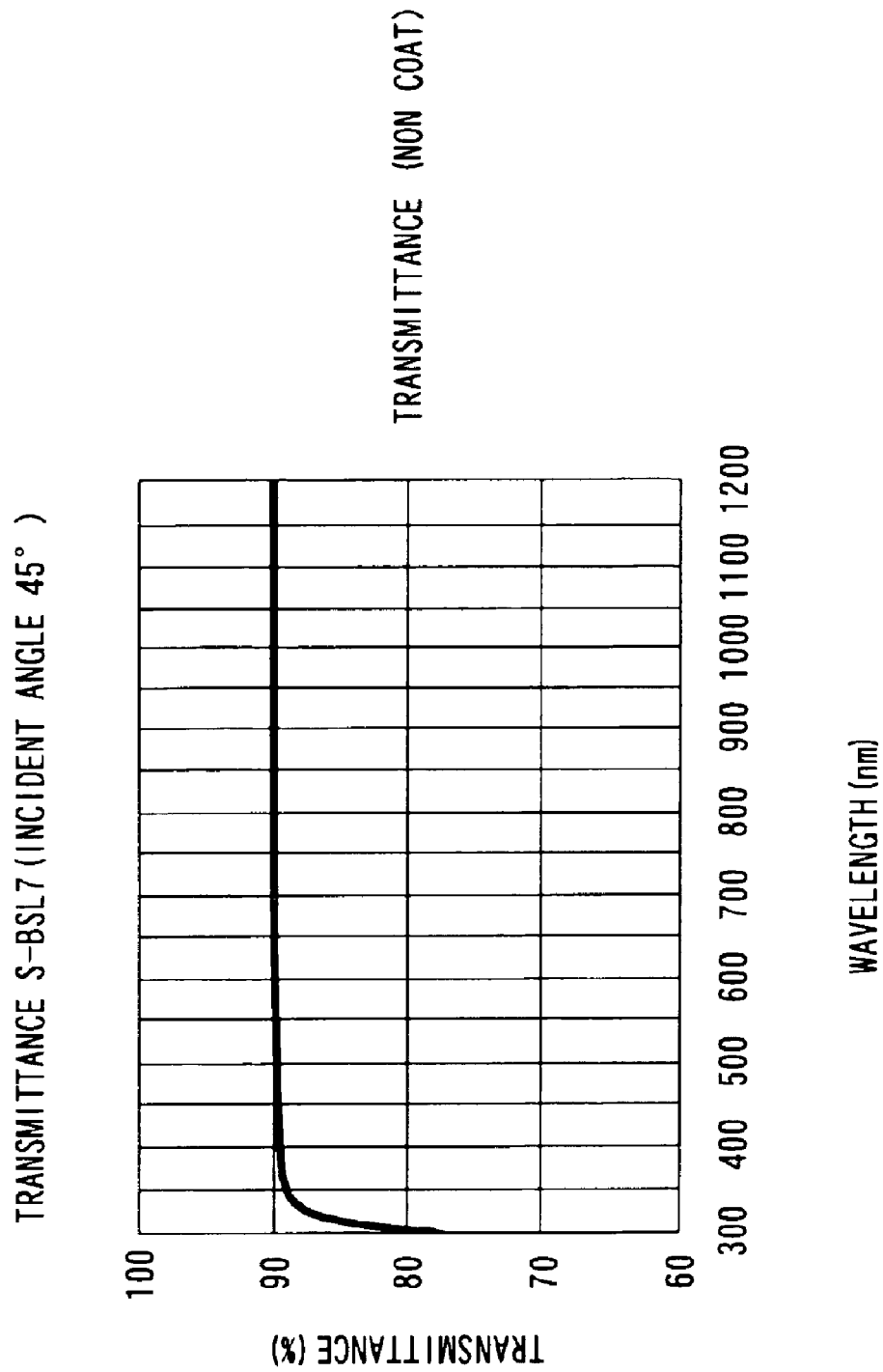
FIG. 3 is a diagram showing an example of the spectral transmittance characteristic of a light splitter.
Figure 4:
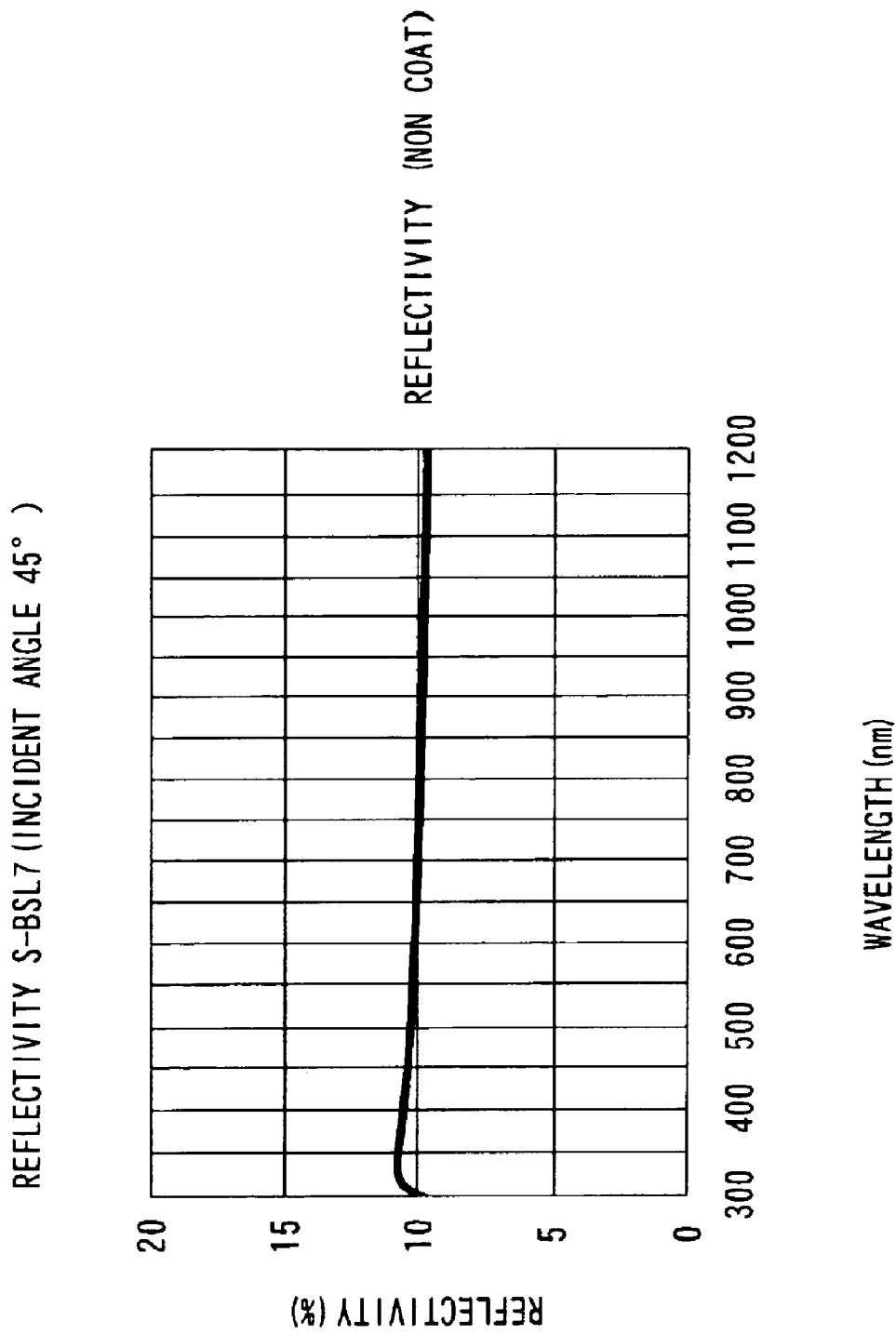
FIG. 4 is a diagram showing an example of the spectral reflectivity characteristic of the light splitter.

The light splitter 5 in the first embodiment is a so-called dichroic mirror that has the spectral transmittance characteristics mentioned above. Also, a plane-parallel plate using Type S-BSL7 (made by OHARA INC.) as a glass substrate can be used as the light splitter 5. In this case, it is desirable that, as shown in FIGS. 3 and 4, the plane-parallel plate has the spectral transmittance characteristics that the transmittance is above 85% and the reflectivity is below 15% in a 400–700 nm wavelength region.

The second wavelength selective member 7 is an optical element, usually called an absorption filter, and has preset spectral transmittance characteristics. The second wavelength selective member 7 is placed in the optical path and thereby can be transparent to only the fluorescent light, of the fluorescent light and the excitation light. The fluorescent light passing through the second wavelength selective member 7 forms a fluorescent image at a preset position through the imaging lens 8. When an eyepiece is placed in the proximity of the fluorescent image, the fluorescent image can be observed by visual view. However, the fluorescent image in the first embodiment, as described later, is dark. It is thus desirable that an electronic image sensor, such as a cooling CCD, notably a high-sensitivity image sensor, is placed for image formation.

Figure 5:
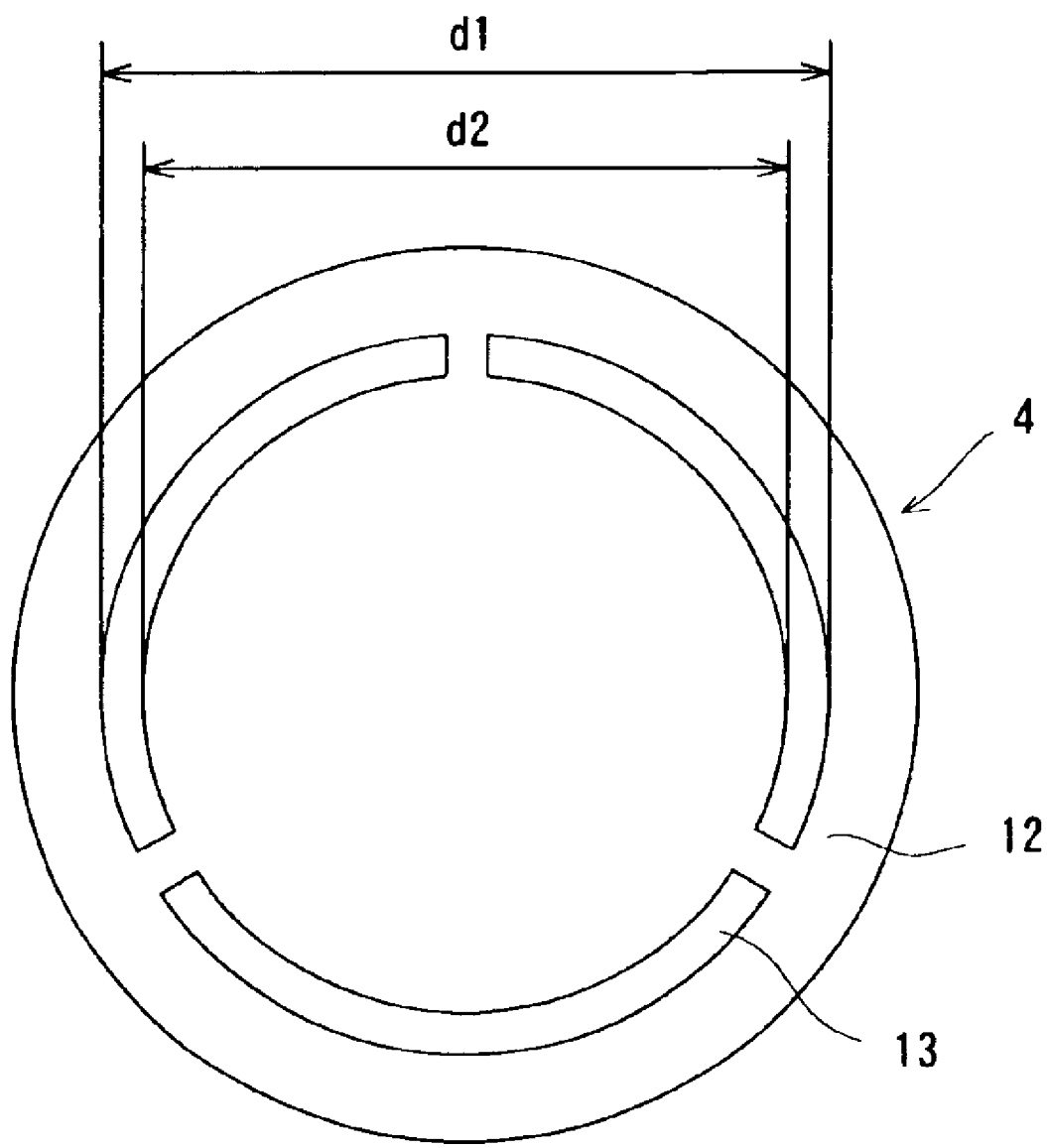
FIG. 5 is a view showing the structure of the aperture member.

Subsequently, reference is made to light emerging from the aperture member 4. The aperture member 4, as shown in FIG. 1 or 2, is located at the conjugate position 2a relative to the pupil position 6a of the objective lens 6. As shown in FIG. 5, the aperture member 4 has a light-blocking section 12 blocking light and a light-transmitting section 13 (a partial aperture) transmitting light. In FIG. 5, d1 represents the outside diameter of the light-transmitting section 13 and d2 represents the inside diameter of the light-transmitting section 13. In the first embodiment, the irradiation light passes through space between the diameters d1 and d2. Therefore, a ray passing through the boundary between the light-blocking section 12, lying at a distance of d1/2 from the optical axis, and the light-transmitting section 13 is the one farthest from the optical axis, of rays passing through the light-transmitting section 13; that is, the outer ray. On the other hand, a ray passing through the boundary between the light-blocking section 12, lying at a distance of d2/2 from the optical axis, and the light-transmitting section 13 is the one closest to the optical axis, of rays passing through the light-transmitting section 13, that is, the inner ray.

In the first embodiment, an opaque material is provided with the light-transmitting section 13. Thus, the light-transmitting section 13 is divided into three openings. Also, the light-blocking section 12 may be formed in such a way that, for example, metal is evaporated on a transparent material, such as plane-parallel plate glass, (or the transparent material is coated with metal).

In the first embodiment, since the aperture member 4 is placed in the illumination optical system 2, the light emerging from the aperture member 4 assumes an annular shape. The annular light passes through the first wavelength selective member 3 and is reflected by the light splitter 5 to enter the objective lens 6. The light is condensed at the pupil position 6a of the objective lens 6, where the image of the aperture member 4 is formed. The light then emerges from the objective lens 6 and reaches the specimen 11, which is illuminated in a preset range.

Figure 6:
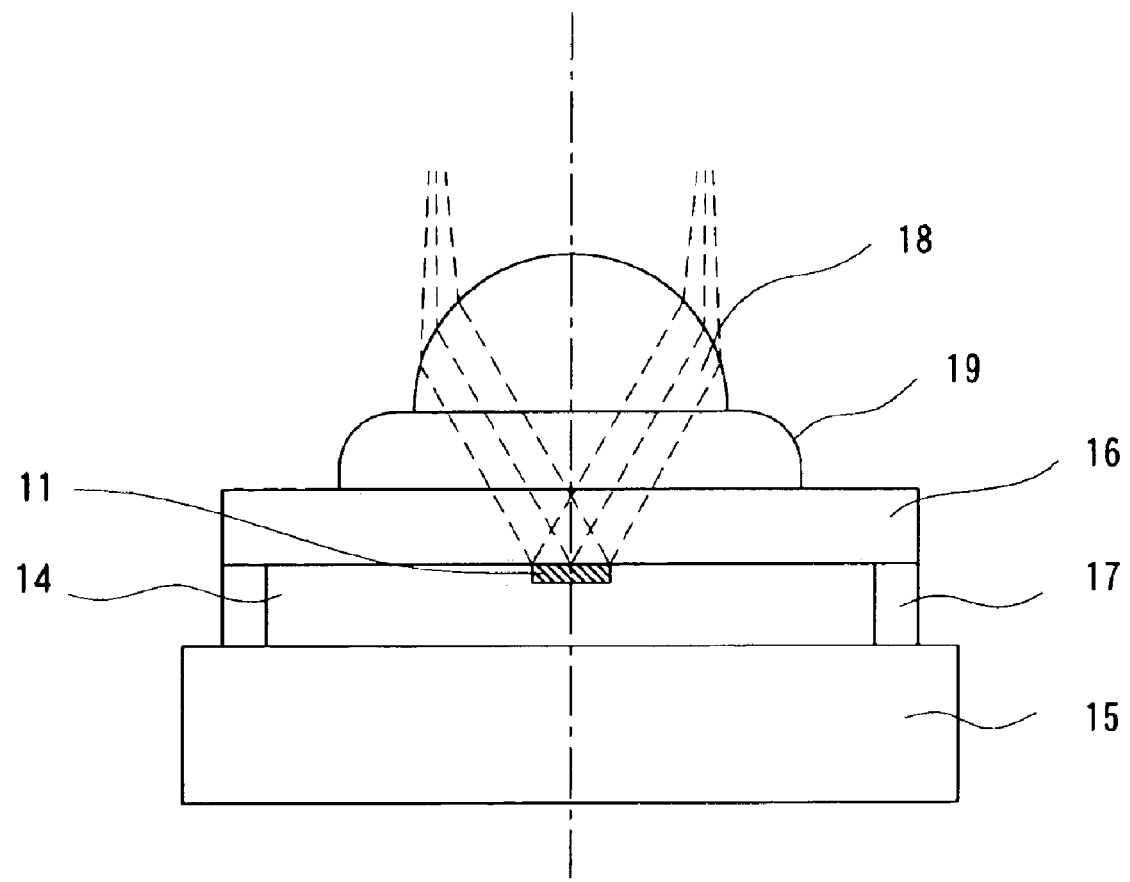
FIG. 6 is a view showing a state where a specimen is held.

The specimen 11, as shown in FIG. 6, is held together with a medium 14. Since the medium 14 is a liquid in most cases, a spacer is sandwiched between a slide glass 15 and a cover glass 16 to form space. The medium 14 (as well as the specimen 11) is enclosed in this space. In the first embodiment, the medium 14 is water ($n_1$=1.33304). Reference numeral 18 represents the tip lens portion of the objective lens 6. Since the objective lens 6 used in the first embodiment is an immersion lens, an immersion oil 19 is provided between the tip lens portion 18 and the cover glass 16.

The objective lens 6 used in the first embodiment is the one disclosed in Japanese Patent Kokai No. Hei 6-160720, and has a magnification of 40×, a numerical aperture (NA) of 1.0, and a focal length of 4.5 mm. The projection magnification of the optical system interposed between the conjugate position 2a where the aperture member 4 is located and the pupil position 6a of the objective lens 6 is 2×. The outside diameter d1 of the light-transmitting section 13 of the aperture member 4 is 4.5 mm and the inside diameter d2 is 2.5 mm.

Thus, the following dimensions are obtained:
Pupil diameter L of objective lens 6=2×1.0×4.5=9 mm
Outside diameter D1 of light-transmitting section 13 projected on pupil surface 6a of objective lens 6=9 mm
Inside diameter D2 of light-transmitting section 13 projected on pupil surface 6a of objective lens 6=5 mm
That is, the annular light that the inside diameter is 5 mm and the outside diameter is 9 mm is collected on the specimen 11 while converging. Here, numerical apertures derived from angles made by the annular light, namely the inner ray and the outer ray, with the optical axis of the objective lens are as follows:
Numerical aperture $NA_1$ of inner ray=5/(2×4.5)=0.56
Numerical aperture $NA_2$ of outer ray=9/(2×4.5)=1.0
That is, only excitation light with a numerical aperture of 0.56–1.0 passes through the objective lens 6.

For example, when d1=4.5 mm and d2=3.5 mm, the dimensions and numerical apertures are as follows:
Outside diameter D1 of light-transmitting section 13 projected on pupil surface 6a of objective lens 6=9 mm
Inside diameter D2 of light-transmitting section 13 projected on pupil surface 6a of objective lens 6=7 mm
Numerical aperture $NA_1$ of inner ray=7/(2×4.5)=0.78
Numerical aperture $NA_2$ of outer ray=9/(2×4.5)=1.0

Figure 7:
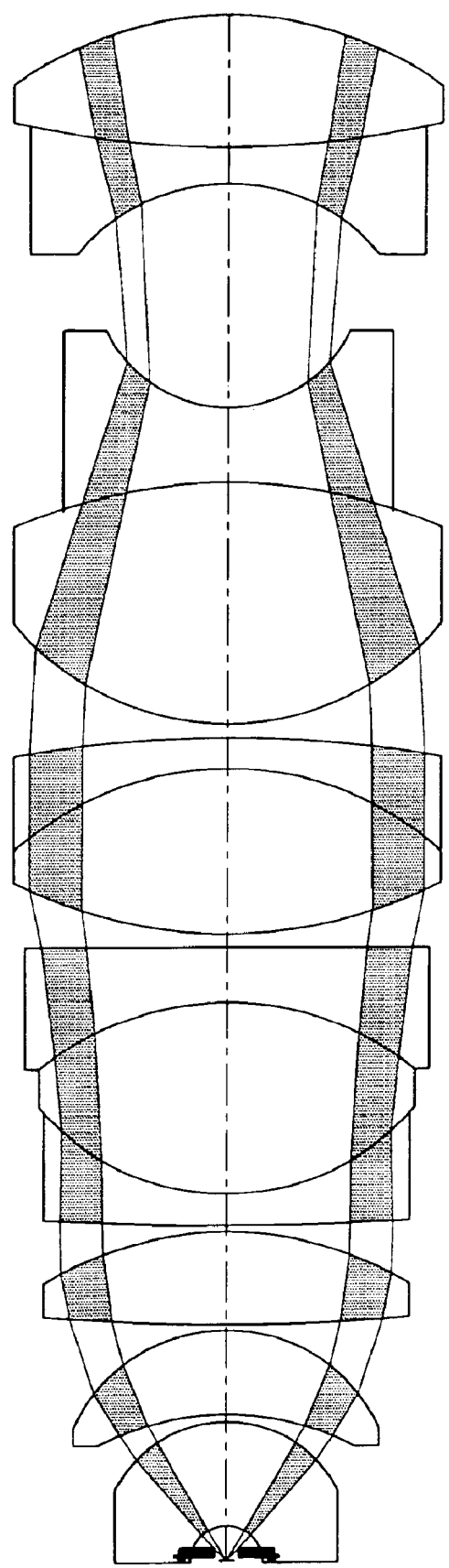
FIG. 7 is a view showing a state where the light emerging from the aperture member passes through an objective lens.

A state where the annular light passes through the objective lens 6 is illustrated in FIG. 7. A ray diagram depicted in FIG. 7 corresponds to the case where the aperture member of d1=4.5 mm and d2=3.5 mm is used. In this case, as seen from the above calculations, excitation light with a numerical aperture of 0.78–1.0 passes through the objective lens 6. As described above, when the aperture member 4 is placed, the excitation light passes through only the periphery of the objective lens 6. Consequently, the production of auto fluorescence from glass used for the objective lens 6 can be held to a minimum.

In the first embodiment, the objective lens such that the magnification is 40× and the numerical aperture is 1.0 is often constructed with convex lens elements of small curvature. In this case, as the position of passage of the excitation light approaches the periphery of the lens, the volume of the lens is decreased. Consequently, the production of auto fluorescence can be held to a minimum. The auto fluorescence is produced from the periphery and thus is multi-reflected by a lens frame. Hence, the auto fluorescence returned to the observation side becomes very little.

This, in contrast with conventional reflection fluorescence illumination (illumination such that excitation light passes through an almost entire pupil surface of the objective lens 6), excels in the fact that the absolute amount of auto fluorescence can be held. It is avoidable that, as in the conventional illumination, auto fluorescence is produced at the lens center (this auto fluorescence is liable to be returned to the observation side). Moreover, even in the objective lens with the numerical aperture above 1.0, there is no need to irradiate the specimen with excitation light from the outside of the objective lens.

As discussed above, a reduction of the production of auto fluorescence, which formerly has been difficult, can be easily achieved by the construction of the first embodiment. Furthermore, according to the first embodiment, a great deal of excitation light is blocked by the light-blocking section of the aperture member. Consequently, the intensity of excitation light irradiating the specimen can be extremely lowered, without requiring a conventional attenuation filter. Damage to the specimen can thus be reduced at the same time. According to the first embodiment, as mentioned above, an extremely high-sensitivity fluorescence observation apparatus that has a relatively simple structure and is most suitable for the clarification of the biological functions of the living cells can be provided.

Second Embodiment

The basic arrangement of the second embodiment is the same as in FIG. 1. In this embodiment, the objective lens 6 is the one disclosed in Japanese Patent Kokai No. Hei 7-35983, and has a magnification of 60×, a numerical aperture (NA) of 1.4, and a focal length of 3 mm. The projection magnification of the optical system interposed between the conjugate position 2a where the aperture member 4 is located and the pupil position 6a of the objective lens 6 is 2×. The outside diameter d1 of the light-transmitting section 13 of the aperture member 4 is 4.5 mm and the inside diameter d2 is 3 mm.

Thus, the following dimensions are obtained:

Pupil diameter L of objective lens $6 = 2 \times 1.4 \times 3 = 8.4$ mm

Outside diameter D1 of light-transmitting section 13 projected on pupil surface 6a of objective lens 6 = 9 mm Inside diameter D2 of light-transmitting section 13 projected on pupil surface 6a of objective lens 6 = 6 mm That is, the annular light that the inside diameter is 6 mm and the outside diameter is 9 mm is collected on the specimen 11 while converging. Here, numerical apertures derived from angles made by the annular light with the optical axis are as follows:

Numerical aperture $NA_1$ of inner ray $= 6/(2 \times 3) = 1.0$

Numerical aperture $NA_2$ of outer ray $= 9/(2 \times 3) = 1.5$

Here, the numerical aperture $NA_2$, when being 1.5, exceeds the maximum numerical aperture NA of 1.4 of the objective lens. Thus, the light beam is substantially limited by the frame of the objective lens and the numerical aperture $NA_2$ becomes 1.4. That is, only excitation light with a numerical aperture of 1.0–1.4 passes through the objective lens 6.

The objective lens that the magnification is 60× and the numerical aperture is 1.4, used in the second embodiment, is also often constructed with convex lens elements of small curvature as described in the first embodiment. Thus, the objective lens is transparent to only excitation light of large numerical aperture, and thereby the production of auto fluorescence can be held to a minimum.

Figure 8:
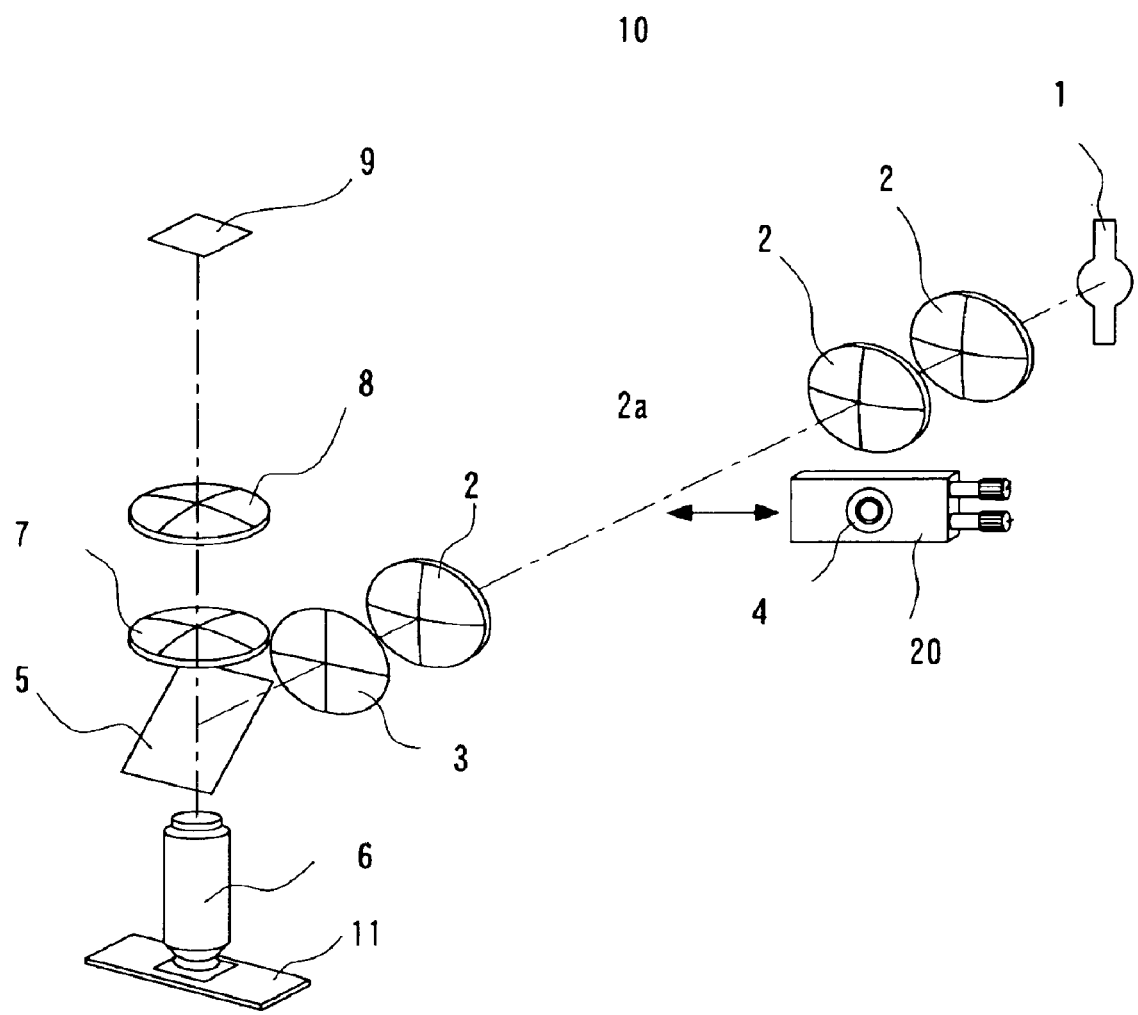
FIG. 8 is a view showing that the aperture member is movable in and out of an illumination optical path in the fluorescence observation apparatus of the present invention.

The aperture member 4, as illustrated in FIG. 8, can also be constructed so that it is sustained by a holder 20. In this case, it is only necessary that the aperture member 4 is constructed to be movable in and out of the optical path for illumination. By doing so, a technique called photo bleaching can be used in which the specimen is intentionally irradiated with strong excitation light and fluorescent light is bleached. This photo-bleaching technique utilizes a phenomenon that protein labeled by fluorescence from a bleached periphery is diffused and moved so that a state where a fluorescence intensity is gradually increased is observed to thereby clarify an information transmitting function between cells.

Third Embodiment

The arrangement of the third embodiment is also the same as in the first embodiment. Only the dimensions of the outside and inside diameters of the light-transmitting section 13 are different from those of the second embodiment. The outside diameter d1 of the light-transmitting section 13 of the aperture member 4 is 3.9 mm and the inside diameter d2 is 3.3 mm.

Thus, the following dimensions are obtained:

Pupil diameter L of objective lens $6 = 2 \times 1.4 \times 3 = 8.4$ mm

Outside diameter D1 of light-transmitting section 13 projected on pupil surface 6a of objective lens 6 = 7.8 mm Inside diameter D2 of light-transmitting section 13 projected on pupil surface 6a of objective lens 6 = 6.6 mm That is, the annular light that the inside diameter is 6.6 mm and the outside diameter is 7.8 mm is collected on the specimen 11 while converging. Here, numerical apertures derived from angles made by the annular light with the optical axis are as follows:

Numerical aperture $NA_1$ of inner ray $= 6.6/(2 \times 3) = 1.1$

Numerical aperture $NA_2$ of outer ray $= 7.8/(2 \times 3) = 1.3$

That is, only excitation light with a numerical aperture of 1.1–1.3 passes through the objective lens 6.

In this case, the numerical aperture where excitation light passes through the objective lens is smaller than the refractive index (1.33304) of the medium 14 (water) holding the specimen 11. At the boundary between the medium and the cover glass 16, excitation light does not undergo total reflection. That is, there is little excitation light returned to the objective lens side. As such, the phenomenon that a background noise is produced, attributable to the excitation light returned to the objective lens side, is not caused. Thus, in the third embodiment, any excitation light passes through the specimen 11, and therefore a higher-sensitivity fluorescence observation becomes possible.

Also, although reference has been made to the upright microscope in each of the embodiments, it is needless to say that the present invention is applicable to an inverted microscope. In this case also, the same effect as in the above description is brought about.

What is claimed is:

1. A fluorescence observation apparatus comprising:

a light source;

an illumination optical system conducting irradiation light from the light source to a specimen;

an aperture member provided in the illumination optical system;

a first wavelength selective member;

a light splitter deflecting the irradiation light to conduct the light to the specimen;

an objective lens interposed between the light splitter and the specimen;

a second wavelength selective member transmitting fluorescent light emanating from the specimen; and a detecting device receiving the fluorescent light, wherein the aperture member has a partial aperture through which part of the irradiation light passes, and the fluorescence observation apparatus is provided with a projection optical system projecting the aperture member at a pupil position of the objective lens so that a size of the partial aperture and a magnification of the projection optical system are set to satisfy the following Conditions:

$$0.5NA \leq NA_1 < NA$$

$$NA_1 < n$$

where $NA_1$ is a numerical aperture derived from an angle made by a ray closest to an optical axis, of rays of light passing through the partial aperture, with the optical axis on the specimen, NA is a maximum numerical aperture of the objective lens, and n is a refractive index of a medium holding the specimen.

2. A fluorescence observation apparatus comprising:

a light source;

an illumination optical system conducting irradiation light from the light source to a specimen;

an aperture member provided in the illumination optical system;

a first wavelength selective member;

a light splitter deflecting the irradiation light to conduct the light to the specimen;

an objective lens interposed between the light splitter and the specimen;

a second wavelength selective member transmitting fluorescent light emanating from the specimen; and a detecting device receiving the fluorescent light, wherein the aperture member has a partial aperture through which part of the irradiation light passes, and the fluorescence observation apparatus is provided with a projection optical system projecting the aperture member at a pupil position of the objective lens so that a size of the partial aperture and a magnification of the projection optical system are set to satisfy the following Conditions:

$$0.5NA \leq NA_1 < 0.95NA$$

$$NA_1 < NA_2 \leq NA$$

where $NA_1$ is a numerical aperture derived from an angle made by a ray closest to an optical axis, of rays of light passing through the partial aperture, with the optical axis on the specimen, NA is a maximum numerical aperture of the objective lens, and $NA_2$ is a numerical aperture derived from an angle made by a ray farthest from the optical axis, of rays of light passing through the partial aperture, with the optical axis on the specimen.

3. A fluorescence observation apparatus comprising:

a light source;

an illumination optical system conducting irradiation light from the light source to a specimen;

an aperture member provided in the illumination optical system;

a first wavelength selective member;

a light splitter deflecting the irradiation light to conduct the light to the specimen;

an objective lens interposed between the light splitter and the specimen;

a second wavelength selective member transmitting fluorescent light emanating from the specimen; and a detecting device receiving the fluorescent light, wherein the aperture member has a partial aperture through which part of the irradiation light passes, and the fluorescence observation apparatus is provided with a projection optical system projecting the aperture member at a pupil position of the objective lens so that a size of the partial aperture and a magnification of the projection optical system are set to satisfy the following Conditions:

$$0.75NA \leq NA_1 < NA$$

$$NA_1 < n$$

where $NA_1$ is a numerical aperture derived from an angle made by a ray closest to an optical axis, of rays of light passing through the partial aperture, with the optical axis on the specimen, NA is a maximum numerical aperture of the objective lens, and n is a refractive index of a medium holding the specimen.

4. A fluorescence observation apparatus according to any one of claims 1–3, wherein a shape of the partial aperture is annular.

5. A fluorescence observation apparatus according to claim 2, further satisfying the following condition:

$$NA_2 < n$$

where n is a refractive index of a medium holding the specimen.

6. A fluorescence observation apparatus according to claim 1, further satisfying the following condition:

$$0.1 \leq NA_2 - NA_1$$

where $NA_2$ is a numerical aperture derived from an angle made by a ray farthest from the optical axis, of rays of light passing through the partial aperture, with the optical axis on the specimen.

7. A fluorescence observation apparatus according to claim 3 or 5, wherein the objective lens has a numerical aperture above 1.0.

8. A fluorescence observation apparatus according to claim 3 or 5, wherein the objective lens has an numerical aperture above 1.35.

9. A fluorescence observation apparatus according to any one of claims 1–3, wherein the aperture member is constructed to be movable in and out of the illumination optical system.

10. A fluorescence illumination apparatus comprising:

a light source;

an illumination optical system conducting irradiation light from the light source to a specimen;

an aperture member provided in the illumination optical system;

a first wavelength selective member; and a light splitter deflecting the irradiation light to conduct the light to the specimen, wherein the aperture member has a partial aperture through which part of the irradiation light passes, and the fluorescence illumination apparatus is provided with a projection optical system projecting the aperture member at a pupil position of an objective lens so that a size of the partial aperture and a magnification of the projection optical system are set to satisfy the following Conditions:

$$0.5NA \leq NA_1 < NA$$

$$NA_1 < n$$

where $NA_1$ is a numerical aperture derived from an angle made by a ray closest to an optical axis, of rays of light passing through the partial aperture, with the optical axis on the specimen, NA is a maximum numerical aperture of the objective lens, and n is a refractive index of a medium holding the specimen.

* * * * *